United States Patent
Ascheman et al.

(10) Patent No.: US 9,958,373 B2
(45) Date of Patent: May 1, 2018

(54) PROTOCOL ADAPTIVE COMPUTER CONTROLLED TARGET-ANALYTE PERMEATION TESTING INSTRUMENT

(71) Applicant: MOCON, INC., Minneapolis, MN (US)

(72) Inventors: Timothy A Ascheman, Elk River, MN (US); Stephen D. Tuomela, Ramsey, MN (US)

(73) Assignee: MOCON, INC., Minneapolis, MN (US)

( * ) Notice: Subject to any disclaimer, the term of this patent is extended or adjusted under 35 U.S.C. 154(b) by 143 days.

(21) Appl. No.: 15/038,810

(22) PCT Filed: Feb. 24, 2015

(86) PCT No.: PCT/US2015/017259
§ 371 (c)(1),
(2) Date: May 24, 2016

(87) PCT Pub. No.: WO2015/127430
PCT Pub. Date: Aug. 27, 2015

(65) Prior Publication Data
US 2017/0030820 A1     Feb. 2, 2017

Related U.S. Application Data

(60) Provisional application No. 61/943,772, filed on Feb. 24, 2014.

(51) Int. Cl.
*G01N 15/08* (2006.01)
*G01N 35/00* (2006.01)
*G01N 33/00* (2006.01)

(52) U.S. Cl.
CPC ....... *G01N 15/0826* (2013.01); *G01N 33/004* (2013.01); *G01N 35/00693* (2013.01); *G01N 35/00712* (2013.01); *G01N 2015/086* (2013.01)

(58) Field of Classification Search
CPC .... G01N 15/00; G01N 15/08; G01N 15/0826; G01N 33/00; G01N 33/004; G01N 35/00;
(Continued)

(56) References Cited

U.S. PATENT DOCUMENTS 3,590,634 A * 7/1971 Pasternak ............... G01N 15/08
374/54
4,656,865 A * 4/1987 Callan ................... G01N 15/08
73/38
(Continued)

FOREIGN PATENT DOCUMENTS

CA      2432452 A1    6/2002
EP      2113764 A2    11/2009
(Continued)

OTHER PUBLICATIONS

"Thermo Environmental Instruments Model 48C Trace Level Gas Filter Correlation Carbon Monoxide Analyzer", Standard Operating Procesures, SOP Version No. 2.0, May 6, 2009, p. 1-32.
(Continued)

*Primary Examiner* — Nguyen Ha
(74) *Attorney, Agent, or Firm* — Sherrill Law Offices, PLLC

(57) ABSTRACT

A protocol adaptive, computer controlled target-analyte permeation testing instrument, capable of self-adaptive adjustments to measurement interval, rezero frequency and independent zero go-no-go.

35 Claims, 5 Drawing Sheets

(58) Field of Classification Search
CPC ....... G01N 35/00693; G01N 35/00712; G01N 2015/086; G01M 3/00; G01M 3/20; G01M 3/22
See application file for complete search history.

(56) References Cited

U.S. PATENT DOCUMENTS

| | | | |
|---|---|---|---|
| 4,667,153 | A | 5/1987 | Doyle |
| 4,944,180 | A | 7/1990 | Tou et al. |
| 5,361,625 | A * | 11/1994 | Ylvisaker ............ G01N 15/082 73/38 |
| 6,066,243 | A | 5/2000 | Anderson et al. |
| 7,178,384 | B2 | 2/2007 | Bujas et al. |
| 7,571,749 | B2 | 8/2009 | Stochi |
| 2002/0045243 | A1 | 4/2002 | Laska et al. |
| 2003/0019747 | A1 | 1/2003 | Saffell et al. |
| 2003/0074945 | A1 | 4/2003 | Engle et al. |
| 2005/0211572 | A1 | 9/2005 | Buck et al. |
| 2008/0060418 | A1 | 3/2008 | DeRoos et al. |
| 2010/0054998 | A1 | 3/2010 | Mayer et al. |
| 2010/0223979 | A1 * | 9/2010 | Ploehn ............... G01N 15/0826 73/38 |
| 2010/0274515 | A1 | 10/2010 | Hoss et al. |
| 2012/0262298 | A1 | 10/2012 | Bohm et al. |
| 2012/0330596 | A1 | 12/2012 | Kouznetsov |
| 2014/0238101 | A1 * | 8/2014 | Mealy, Jr. ............ G01N 33/007 73/1.06 |
| 2017/0072157 | A1 * | 3/2017 | Tolmie ............... G01N 33/0006 |

FOREIGN PATENT DOCUMENTS

| | | |
|---|---|---|
| WO | 98/03868 | 1/1998 |
| WO | 2010029282 A2 | 4/2001 |

OTHER PUBLICATIONS

Beyer, David Stewart; "Industrial Accident Prevention"; Book; Houghton Mifflin Company, Boston and New York; 1916.

* cited by examiner

PROTOCOL ADAPTIVE COMPUTER CONTROLLED TARGET-ANALYTE PERMEATION TESTING INSTRUMENT

BACKGROUND

Permeation instruments are used to measure the transmission rate of a target analyte, such as oxygen, carbon dioxide or water vapor, through various samples, such as membranes, films, envelopes, bottles, packages, containers, etc. (hereinafter collectively referenced as "test films" for convenience). Typical test films are polymeric packaging films such as those constructed from low density polyethylene (LDPE), high density polyethylene (HDPE), oriented polypropylene (OPP), polyethylene terephthalate (PET), polyvinylidene chrloride (PVTDC), multi-layer polymeric films, etc. Typically, the film to be tested is positioned within a test chamber to sealing separate the chamber into first and second chambers. The first chamber (commonly referenced as the driving or analyte chamber) is filled with a gas containing a known concentration of the target analyte (commonly referenced as a driving gas). The second chamber (commonly referenced as the sensing chamber) is flushed with an inert gas (commonly referenced as a carrier gas) to remove any target analyte from the cell. A sensor for the target analyte is placed in fluid communication with the sensing chamber for detecting the presence of target analyte that has migrated into the sensing chamber from the driving chamber through the test film. Exemplary permeation instruments for measuring the transmission rate of oxygen ($O_2$), carbon dioxide ($CO_2$) and water vapor ($H_2O$) through test films are commercially available from Mocon, Inc. of Minneapolis, Minn. under the designations OXTRAN, PERMATRAN-C and PERMATRAN-W, respectively.

Permeation instruments typically employ either a flow-through method or an accumulation method for sensing the presence of target analyte in the sensing chamber. Briefly, the flow-through method continuously flushes the sensing chamber with inert carrier gas to transport any target analyte that has migrated into the sensing chamber and deliver it to a remotely located target-analyte sensor. The accumulation method intermittently flushes the sensing chamber with inert carrier gas to transport any target analyte that has migrated into the sensing chamber and deliver it to a remotely located target-analyte sensor, thereby allowing target analyte to accumulate in the sensing chamber for accumulation periods between each sensing.

Permeation instruments typically employ a rigorous testing protocol that includes, in addition to periodic sensing of target-analyte concentrations found in the sensing chamber throughout a permeation testing period, periodic rezeroing throughout the permeation testing period and an individual zero upon conclusion of permeation testing period. Such additional measurements significantly increase testing period time but can be critical to ensuring accuracy of the resultant measurements, particularly when the test film is a superior target-analyte barrier and the concentration of target-analyte reaching the sensing chamber is low.

Accordingly, a substantial need exists for a permeation instrument capable of decreasing testing period time without compromising accuracy.

SUMMARY OF THE INVENTION

The invention is a protocol adaptive, computer controlled target-analyte permeation testing instrument.

A first aspect of the invention is a computer controlled target-analyte permeation testing instrument programmed to periodically measure target-analyte transmission rate throughout a permeation testing period employing a sensing period for each measurement, and adjusting duration of the sensing period of future target-analyte transmission rate measurements based upon the value of at least one previous target-analyte transmission rate measurement. The first aspect of the invention will hereinafter be referenced as the "sensing period adaptive instrument" for purposes of convenience.

A second aspect of the invention is a computer controlled target-analyte permeation testing instrument programmed to adjust the frequency of rezeros. In a first embodiment the instrument is programmed to (-) periodically measure target-analyte transmission rate throughout a permeation testing period, (-) periodically rezero the target-analyte sensor throughout the permeation testing period at a predetermined frequency, and (-) bypass a scheduled rezero when the value of at least one previous target-analyte transmission rate measurement exceeds a predetermined threshold value. In a second embodiment the instrument is programmed to (-) periodically measure target-analyte transmission rate throughout a permeation testing period, (-) periodically rezero the target-analyte sensor throughout the permeation testing period, and (-) adjust frequency of future rezeros of the target-analyte sensor based upon the value of at least one previous target-analyte transmission rate measurement. The second aspect of the invention will hereinafter be referenced as the "rezero frequency adaptive instrument" for purposes of convenience.

A third aspect of the invention is a computer controlled target-analyte permeation testing instrument programmed to (-) periodically measure target-analyte transmission rate throughout a permeation testing period, and (-) perform an individual zero of the target-analyte sensor at the conclusion of the permeation testing period when the ascertained target-analyte transmission rate of the test film is below a predetermined threshold value. The third aspect of the invention will hereinafter be referenced as the "individual zero go-no-go adaptive instrument" for purposes of convenience.

A preferred embodiment of the invention is a computer controlled target-analyte permeation testing instrument programmed in accordance with at least two and preferably all three of the inventive aspects.

DETAILED DESCRIPTION OF A PREFERRED EMBODIMENT

Definitions

Figure 1A:
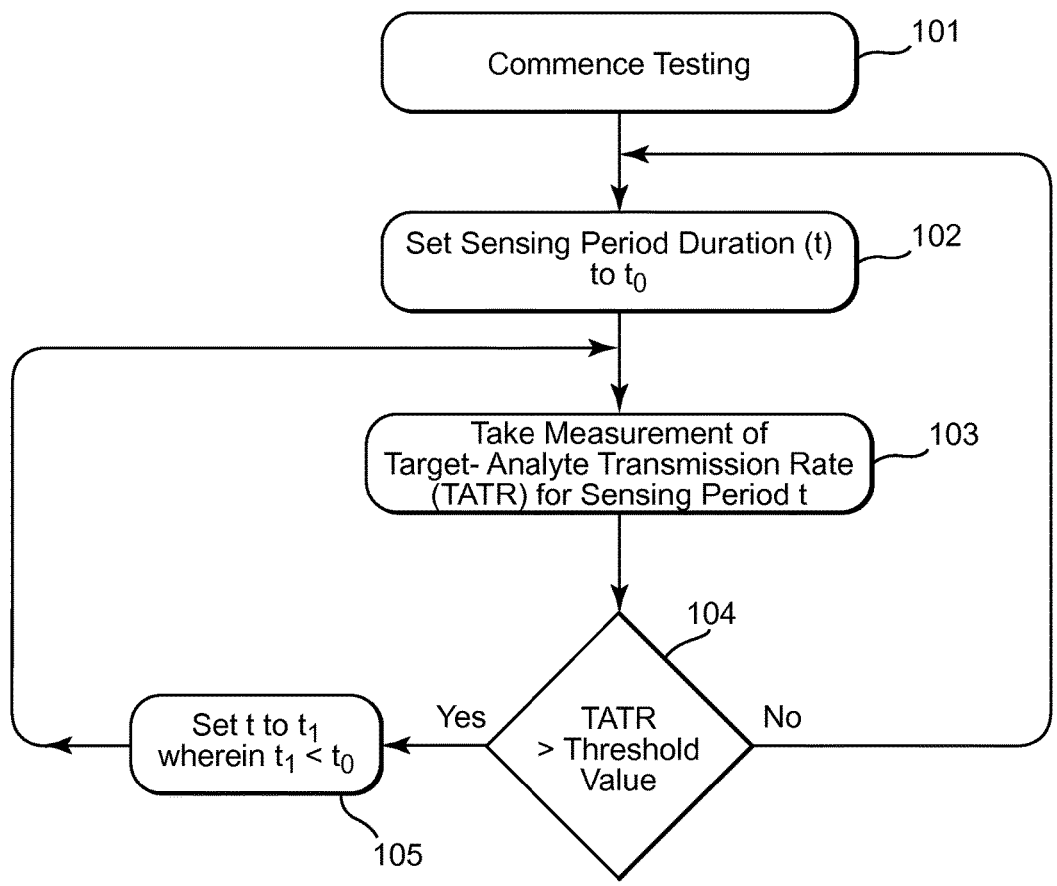
FIG. 1A is a flow diagram of one embodiment of the adaptive sensing period aspect of the invention.

As utilized herein, including the claims, the term "rezero" refers to a method of measuring residual target-analyte contained in the carrier gas of a target-analyte static permeability cell testing instrument during performance of testing that includes the steps of bypassing the test cell(s) and directly measuring the carrier gas target-analyte level which is then subtracted from the measured transmission rate of the target-analyte level for each sample.

As utilized herein, including the claims, the term "individual zero" refers to a method of measuring environmental leakage of a target-analyte static permeability cell testing instrument upon conclusion of a test that includes the steps of eliminating the target-analyte driving force and measuring the carrier gas target-analyte level which then will be subtracted from the transmission rate of the target-analyte level for each sample.

As utilized herein, including the claims, the term "sensing period" refers to a time period during which a target-analyte sensor continuously senses target analyte in a given fluid sample flowing through the sensor from which target-analyte transmission rate is calculated.

Description

Computer controlled target-analyte permeation testing instrument for measuring the transmission rate of a target-analyte, such as oxygen, carbon dioxide or water vapor, through a film are well known and widely used. Typically, the film to be tested is positioned within a test chamber to sealing separate the chamber into first and second chambers. The first chamber (commonly referenced as the driving or analyte chamber) is filled with a gas containing a known concentration of the target analyte (commonly referenced as a driving gas). The second chamber (commonly referenced as the sensing chamber) is flushed with an inert gas (commonly referenced as a carrier gas) to remove any target analyte from the cell. A sensor for the target analyte is placed in fluid communication with the sensing chamber for detecting the presence of target analyte that has migrated into the sensing chamber from the driving chamber through the test film. The various aspects of the invention provide computer-controlled adaptation of the testing protocol employed by the target-analyte permeation testing instrument to ensure selection of a time efficient testing protocol without sacrificing accuracy or reliability of the measurements.

Sensing Period Adaptive Instrument

A first aspect of the invention is a computer controlled target-analyte permeation testing instrument programmed to periodically measure target-analyte transmission rate throughout a permeation testing period and adjust the sensing period of future target-analyte transmission rate measurements based upon the value of at least one previous target-analyte transmission rate measurement. This aspect of the invention eliminates the traditional default of setting the sensing period at some intermediate value, (i.e., 10 minutes) regardless of whether such sensing period is too short so as to potentially affect accuracy of the transmission rate measurement or too long and needlessly monopolizing sensing capacity and/or depleting consumables.

Referring generally to FIG. 1A, the programming for one embodiment of a sensing period adaptive instrument includes the initial traditional steps of commencing testing 101, setting the sensing period t to an initial period of $t_0$ 102, and taking a measurement of target-analyte transmission rate (TATR) for the sensing period t 103.

After at least some and preferably all TATR measurements 103, the TATR measurement is compared in step 104 to a predetermined threshold value. The predetermined threshold value is selected to be indicative of a test film that is highly permeable to the target-analyte, thereby effecting a higher concentration of target-analyte in the carrier gas flowing through the sensing chamber which can be accurately measured with a shorter sensing period. Generally, threshold values of about 0.00025 to 0.025 cc/day for oxygen, 0.025 to 2.5 cc/day for carbon dioxide and 0.000025 to 0.0025 g/day for water vapor are commonly suitable. If the TATR measurement in step 103 is greater than the threshold value, then the sensing period t is reset from to $t_0$ a shorter sensing period of $t_1$ 105, with the expectation that an accurate measurement can be reached with a shorter sensing period, and the cycle repeated. If the TATR measurement in step 103 is less than the threshold value, then the sensing period t is allowed to remain or reset to $t_0$ and the cycle repeated.

Figure 1B:
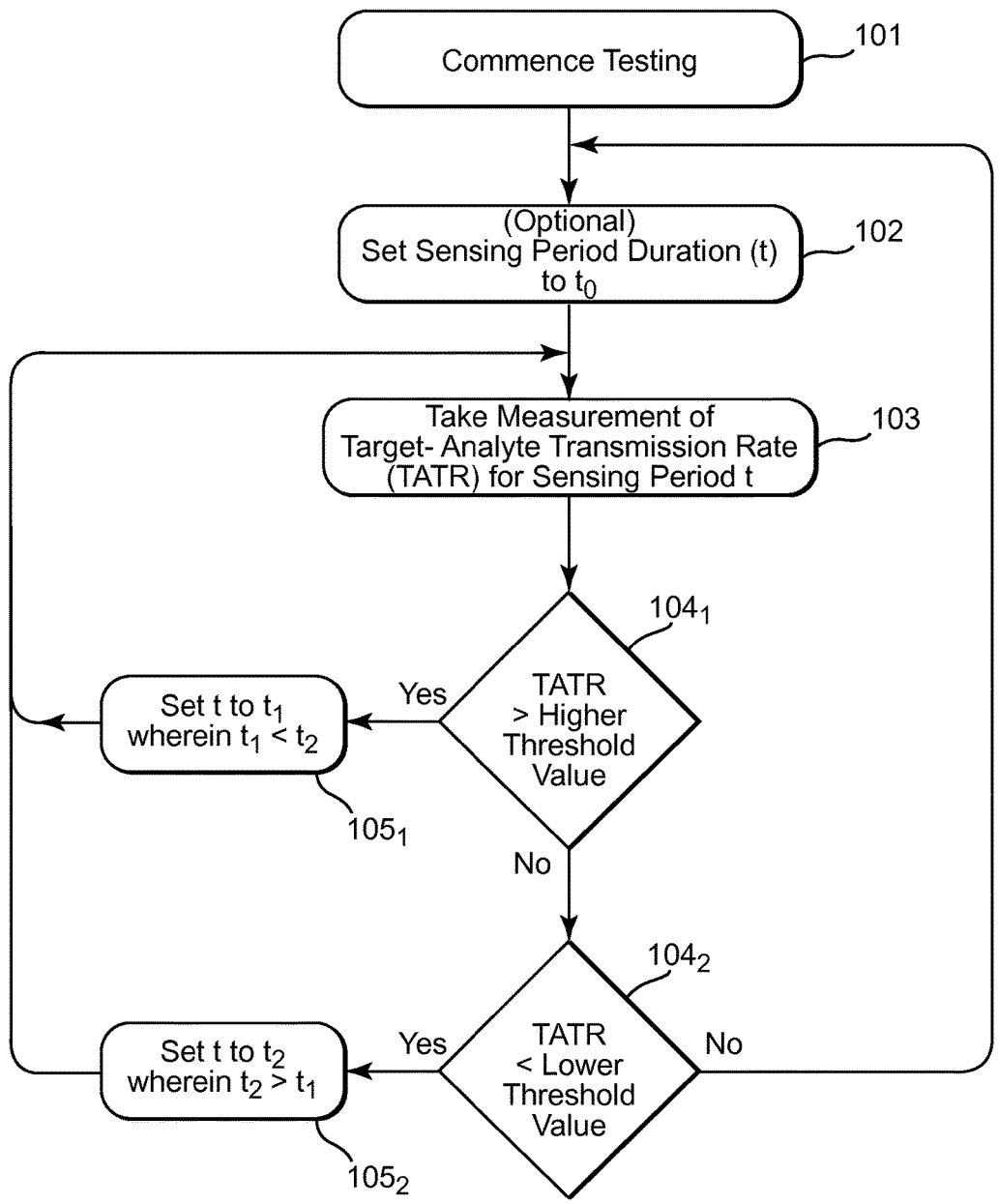
FIG. 1B is a flow diagram of a second embodiment of the adaptive sensing period aspect of the invention.

Referring generally to FIG. 1B, the programming for another embodiment of a sensing period adaptive instrument includes, as with the first embodiment, the initial traditional steps of commencing testing 101, setting the sensing period t to an initial period of $t_0$ 102, and taking a measurement of target-analyte transmission rate (TATR) 103. The step of setting the sensing period t to an initial period of $t_0$ 102, is optional in this embodiment but generally preferred and necessary when the higher threshold value and the lower threshold value are not set at the same value.

After at least some and preferably all TATR measurements 103, as with the first embodiment, the TATR measurement is compared in step $104_1$ to a predetermined higher threshold value. The predetermined higher threshold value is selected to be indicative of a test film that is highly permeable to the target-analyte, thereby effecting a higher concentration of target-analyte in the carrier gas flowing through the sensing chamber which can be accurately measured with a shorter sensing period. If the TATR measurement in step 103 is greater than the higher threshold value, then the sensing period t is set to a shorter sensing period of $t_1$ $105_1$, with the expectation that an accurate measurement can be reached with a shorter sensing period, and the cycle repeated.

If the TATR measurement in step 103 is less than the higher threshold value, then the TATR measurement is compared in step $104_2$ to a predetermined lower threshold value. The predetermined lower threshold value is selected to be indicative of a test film that is minimally permeable to the target-analyte (i.e., a superior target-analyte barrier), thereby effecting a lower concentration of target-analyte in the carrier gas flowing through the sensing chamber which requires a longer sensing period for accurate measurement. If the TATR measurement in step 103 is less than the lower threshold value, then the sensing period t is set to a longer sensing period of $t_2$ $105_2$, with the expectation that a longer sensing period is necessary to obtain an accurate measurement, and the cycle repeated. If the TATR measurement in step 103 is more than the lower threshold value, then the sensing period t is allowed to remain or reset to $t_0$ and the cycle repeated.

Generally, higher threshold values of about 0.00025 to 0.025 cc/day for oxygen, 0.025 to 2.5 cc/day for carbon dioxide and 0.000025 to 0.0025 g/day for water vapor, and lower threshold values of about 0.00025 to 0.025 cc/day for oxygen, 0.025 to 2.5 cc/day for carbon dioxide and 0.000025 to 0.0025 g/day for water vapor, are commonly suitable. When a gap exists between the higher threshold value and the lower threshold value (i.e., these two threshold values are not identical) then an initial sensing period of $t_0$ must be established in step 102 so that a value for the sensing period t exists (i.e., $t_0$) in the event the TATR measurement in step 103 falls within the gap (i.e., less than the higher threshold value and more than the lower threshold value).

The value of the at least one previous target-analyte transmission rate measurement can be the value of the immediately preceding measurement, the mean or median of a plurality of immediately preceding measurements, or some variation thereof such as the mean of the last seven measurements after discarding the high and the low values.

Rezero Frequency Adaptive Instrument

A second aspect of the invention is a computer controlled target-analyte permeation testing instrument programmed to adjust the frequency of rezeros. This aspect of the invention eliminates the traditional default of conducting rezeros on a frequent schedule, (i.e., every other target-analyte transmission rate measurement) regardless of need.

Figure 2A:
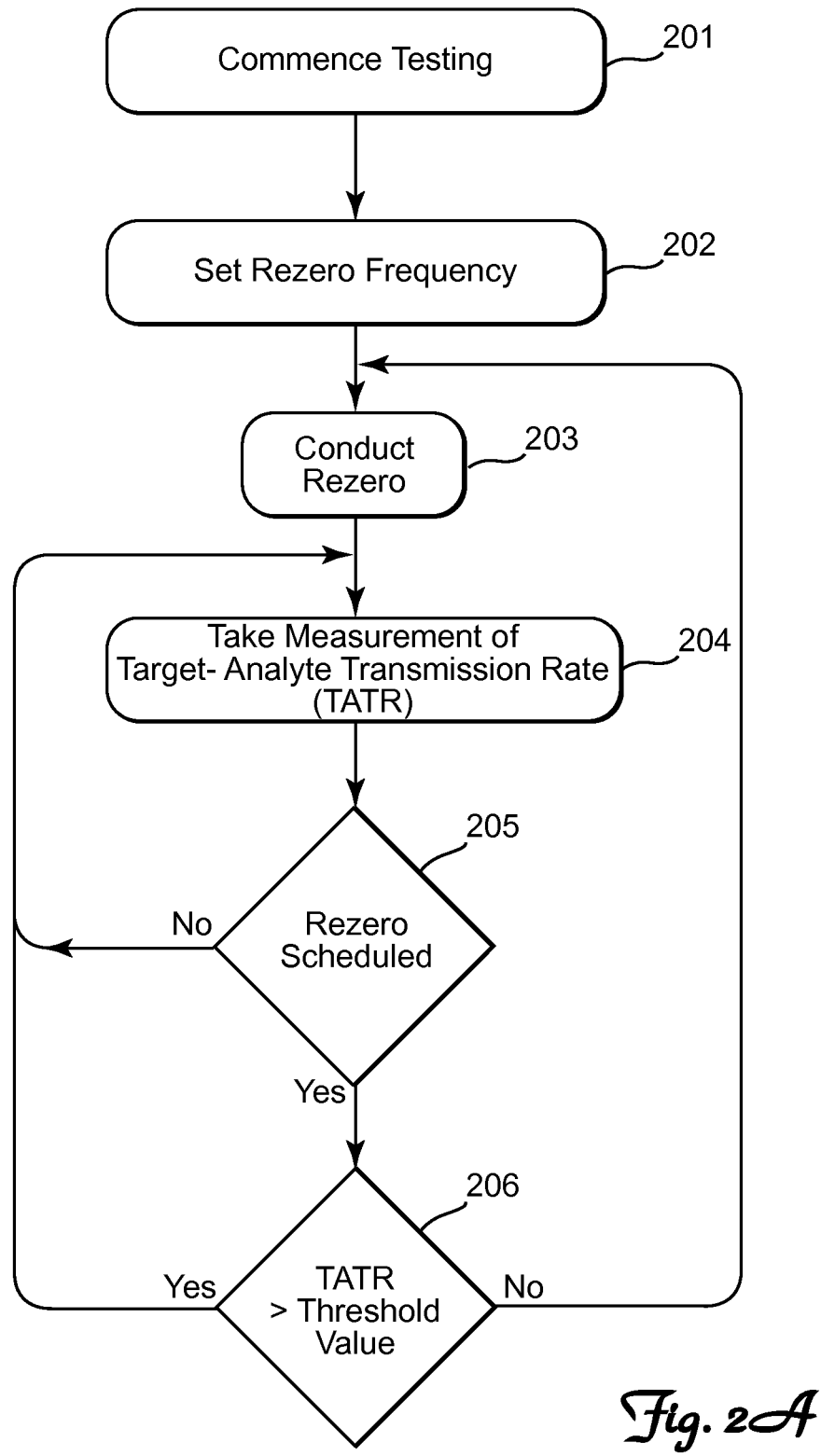
FIG. 2A is a flow diagram of one embodiment of the adaptive rezero frequency aspect of the invention.

Referring generally to FIG. 2A, the programming for one embodiment of a rezero frequency adaptive instrument includes the initial traditional steps of commencing testing 201, setting a rezero frequency $f_0$ 202, conducting a rezero 203, and taking a measurement of target-analyte transmission rate (TATR) 204. The frequency of rezero measurements is typically based upon number of TATR measurements taken (e.g., every other TATR measurement) but can be based upon time.

When a rezero is not scheduled based upon the set rezero frequency $f_0$ 205, the instrument does not conduct a rezero and proceeds to take a subsequent TATR measurement in accordance with a TATR measurement schedule. When a rezero is scheduled based upon the set rezero frequency $f_0$ 205, the TATR measurement is compared in step 206 to a predetermined threshold value. The predetermined threshold value is selected to be indicative of a value that is at least two and preferably at least three orders of magnitude greater than any anticipated target-analyte readings obtained from a rezero measurement such that any rezero adjustments to the final TATR value would be statistically insignificant. Generally, threshold values of about 0.00025 to 0.025 cc/day for oxygen, 0.025 to 2.5 cc/day for carbon dioxide and 0.000025 to 0.0025 g/day for water vapor are commonly suitable for a target-analyte permeation testing instrument and a source of inert carrier gas of reasonable quality and integrity. If the TATR measurement in step 204 is greater than the threshold value, then the instrument does not conduct a rezero and proceeds to take a subsequent TATR measurement in accordance with a TATR measurement schedule. If the TATR measurement in step 204 is less than the threshold value, then a rezero is taken at step 203 before the next TATR measurement is taken in step 204 and the cycle repeated.

Figure 2B:
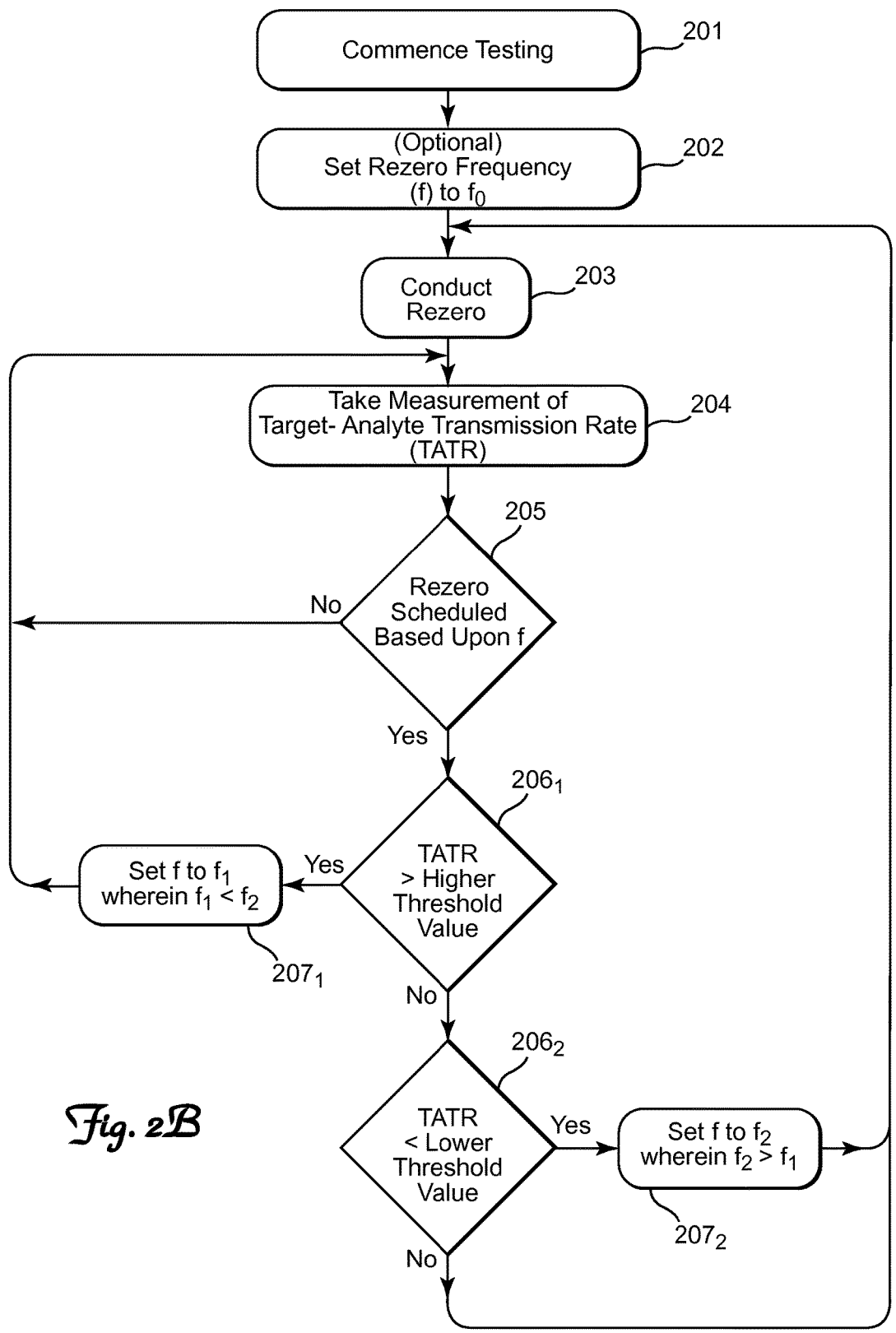
FIG. 2B is a flow diagram a second embodiment of the adaptive rezero frequency aspect of the invention.

Referring generally to FIG. 2B, the programming for another embodiment of a rezero frequency adaptive instrument includes, as with the first embodiment, the initial traditional steps of commencing testing 201, setting a rezero frequency f to an initial interval period of $f_0$ 202, conducting a rezero 203, and taking a measurement of target-analyte transmission rate (TATR) 204. Again, the frequency of rezero measurements is typically based upon number of TATR measurements taken (e.g., every other TATR measurement) but can be based upon time. The step of setting a rezero frequency f to an initial interval period of $f_0$ 202, is optional in this embodiment but generally preferred and necessary when the higher threshold value and the lower threshold value are not set at the same value.

When a rezero is not scheduled based upon the set rezero frequency f 205, the instrument does not conduct a rezero and proceeds to take a subsequent TATR measurement in accordance with a TATR measurement schedule. When a rezero is scheduled based upon the set rezero frequency f 205, the TATR measurement is compared in step $206_1$ to a predetermined higher threshold value. The predetermined threshold value is selected to be indicative of a value that is at least two and preferably at least three orders of magnitude greater than any anticipated target-analyte readings obtained from a rezero measurement such that any rezero adjustments to the final TATR value would be statistically insignificant. If the TATR measurement in step 204 is greater than the higher threshold value, then the frequency f is reset to a less frequent frequency of $f_1$ $207_1$, with the expectation that relaxed control of rezero values will shorten the permeation testing period without any meaningful impact on accuracy.

If the TATR measurement in step 205 is less than the higher threshold value, then the TATR measurement is compared in step $206_2$ to a predetermined lower threshold value. The predetermined lower threshold value is selected to be indicative of a value that is less than at two and preferably the same order of magnitude as any anticipated target-analyte readings obtained from a rezero measurement such that rezero adjustments to the final TATR value would likely be statistically significant. If the TATR measurement in step 204 is less than the lower threshold value, then the frequency f is reset to a more frequent frequency of $f_2$ $207_2$, with the expectation that tighter control of rezero values, while prolonging the permeation testing period, are necessary and appropriate to ensuring accuracy.

Generally, higher threshold values of about 0.00025 to 0.025 cc/day for oxygen, 0.025 to 2.5 cc/day for carbon dioxide and 0.000025 to 0.0025 g/day for water vapor, and lower threshold values of about 0.00025 to 0.025 cc/day for oxygen, 0.025 to 2.5 cc/day for carbon dioxide and 0.000025 to 0.0025 g/day for water vapor, are commonly suitable for a target-analyte permeation testing instrument and a source of inert carrier gas of reasonable quality and integrity. When a gap exists between the higher threshold value and the lower threshold value (i.e., these two threshold values are not identical) then an initial frequency $f_0$ must be established in step 202 so that a value for frequency f exists (i.e., $f_0$) in the event the TATR measurement in step 204 falls within the gap (i.e., less than the higher threshold value and more than the lower threshold value).

The value of the at least one previous target-analyte transmission rate measurement can be the value of the immediately preceding measurement, the mean or median of a plurality of immediately preceding measurements, or some variation thereof such as the mean of the last seven measurements after discarding the high and the low values.

Individual Zero Go-No-Go Adaptive Instrument

A third aspect of the invention is a computer controlled target-analyte permeation testing instrument programmed to periodically measure target-analyte transmission rate throughout a permeation testing period, and perform an individual zero of the target-analyte sensor at the conclusion of the permeation testing period when the ascertained target-analyte transmission rate of the test film is below a predetermined threshold value. This aspect of the invention eliminates the traditional default of conducting an individual zero regardless of need.

Figure 3:
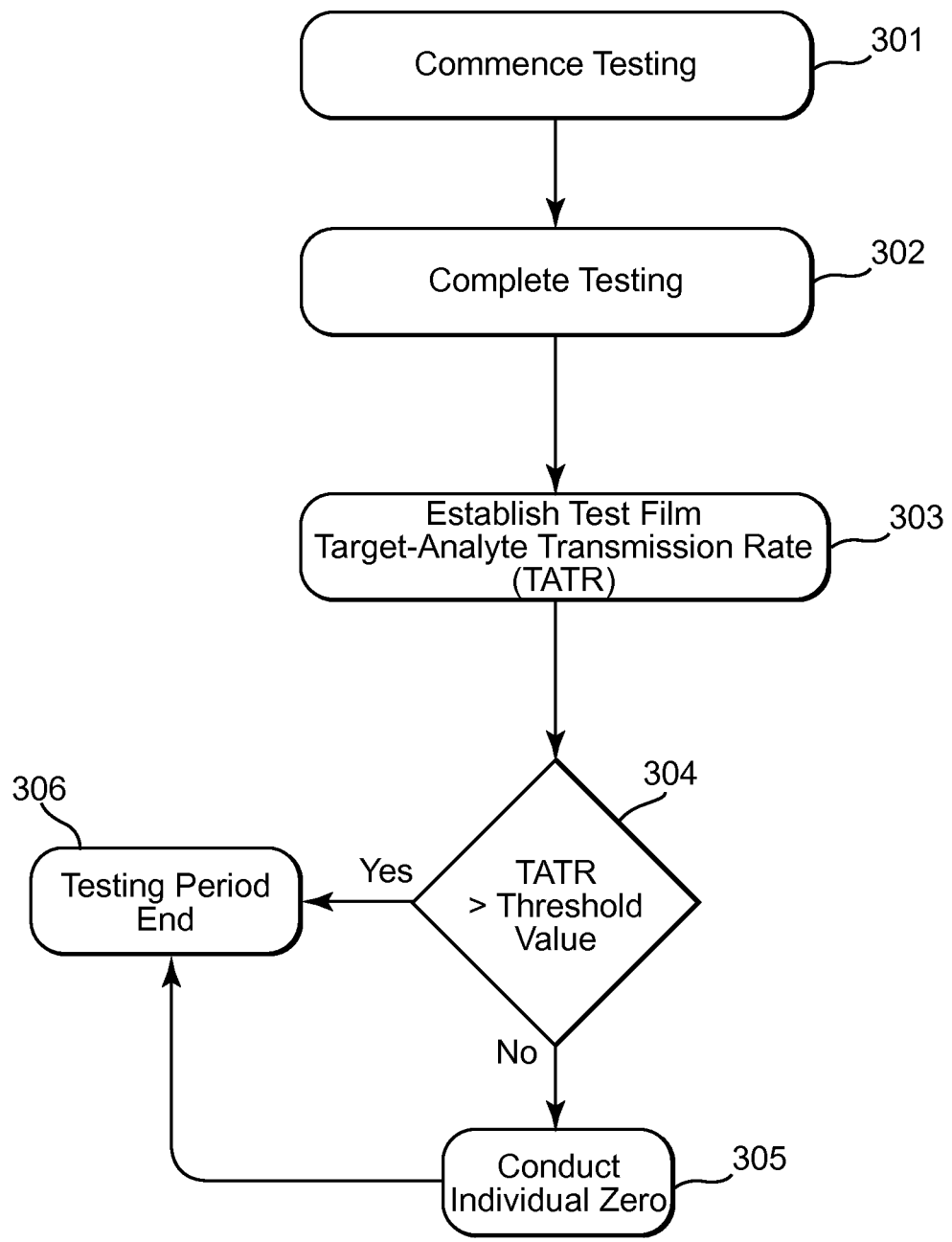
FIG. 3 is a flow diagram of one embodiment of the adaptive go-no-go individual zero aspect of the invention.

Referring generally to FIG. 3, the programming for one embodiment of an individual zero go-no-go adaptive instrument includes the initial traditional steps of commencing testing 301, completing testing 302, and establishing a target-analyte transmission rate (TATR) 303 from the test data.

After completion of testing 302 and establishment of a target-analyte transmission rate (TATR) 303 for the test film, the established TATR value is compared in step 304 to a predetermined threshold value. The predetermined threshold value is selected to be indicative of a value that is at least two and preferably at least three orders of magnitude greater than any anticipated target-analyte readings obtained from an individual zero measurement such that any individual zero adjustment to the established TATR value would be statistically insignificant. Generally, threshold values of about 0.00025 to 0.025 cc/day for oxygen, 0.025 to 2.5 cc/day for carbon dioxide and 0.000025 to 0.0025 g/day for water vapor are commonly suitable for a target-analyte permeation testing instrument and a source of inert carrier gas of reasonable quality and integrity. If the established TATR value in step 303 is greater than the threshold value, then no individual zero is performed and the testing period is ended 306. If the established TATR value in step 303 is less than the threshold value, then an individual zero is performed 305 before the testing period is ended 306.

The ascertained target-analyte transmission rate of the test film can be the value of the final measurement, the mean or median of a plurality of consecutive measurements taken at conclusion of the permeation testing period, or some variation thereof such as the mean of the last seven measurements after discarding the high and the low values.

Testing Procedure

A film to be tested is "loaded" into the testing chamber of one of the cells so as to sealingly separate the testing chamber into a driving chamber and a sensing chamber with a known area of the film exposed to both chambers. First shutoff valves are then opened to permit the flow of inert carrier gas through the sensing chamber for flushing any target-analyte from the sensing chamber. Second shutoff valves are then opened to permit the flow of driving gas—containing a known concentration of target analyte—into the driving chamber. The presence of target analyte within the sensing chamber is then detected and recorded by the target-analyte sensor. By ensuring that the only route through which analyte can enter into the sensing chamber is through the "exposed" area of the film, the rate at which the target analyte sensor detects target analyte, once a steady state rate is attained, can be equated to the analyte transmission rate for the known "exposed" area of the film.

Rezeros are run by temporarily sealing off the flow of inert carrier gas into the sensing chamber and directing inert carrier gas directly to the target-analyte sensor.

Optimal selection of frequency of target-analyte transmission rate measurements, frequency of rezeros, and whether to perform an individual zero are autonomously determined by computer control sans user input.

We claim:

1. An adaptive analytical instrument, comprising a computer controlled target-analyte permeation testing instrument programmed to periodically measure target-analyte transmission rate throughout a permeation testing period employing a sensing period for each measurement, and automatically adjust duration of the sensing period of future target-analyte transmission rate measurements based upon a value of at least one previous target-analyte transmission rate measurement.

2. An adaptive analytical instrument, comprising a computer controlled target-analyte permeation testing instrument programmed to (-) periodically measure target-analyte transmission rate throughout a permeation testing period, (-) periodically rezerothe target-analyte sensor throughout the permeation testing period at a predetermined frequency, and (-) bypass a scheduled rezero when a value of at least one previous target-analyte transmission rate measurement exceeds a predetermined threshold value.

3. An adaptive analytical instrument, comprising a computer controlled target-analyte permeation testing instrument programmed to (-) periodically measure target-analyte transmission rate throughout a permeation testing period, (-) periodically rezero the target-analyte sensor throughout the permeation testing period, and (-) adjust frequency of future rezeros of the target-analyte sensor based upon a value of at least one previous target-analyte transmission rate measurement.

4. An adaptive analytical instrument, comprising a computer controlled target-analyte permeation testing instrument programmed to (-) periodically measure target-analyte transmission rate throughout a permeation testing period, and (-) perform an individual zero of the target-analyte sensor at the conclusion of the permeation testing period when an ascertained target-analyte transmission rate of the test film is below a predetermined threshold value.

5. The adaptive analytical instrument of claim 1, wherein the computer controlled target-analyte permeation testing instrument is further programmed to (-) periodically rezero the target-analyte sensor throughout the permeation testing period at a predetermined frequency, and (-) bypass a scheduled rezero when the value of at least one previous target-analyte transmission rate measurement exceeds a predetermined threshold value.

6. The adaptive analytical instrument of claim 1, wherein the computer controlled target-analyte permeation testing instrument is further programmed to (-) periodically rezero the target-analyte sensor throughout the permeation testing period, and (-) adjust frequency of future rezeros of the target-analyte sensor based upon the value of at least one previous target-analyte transmission rate measurement.

7. The adaptive analytical instrument of claim 1, wherein the computer controlled target-analyte permeation testing instrument is further programmed to perform an individual zero of the target-analyte sensor at the conclusion of the permeation testing period when the final target-analyte transmission rate measurement falls below a predetermined threshold value.

8. The adaptive analytical instrument of claim 1, wherein the target-analyte is oxygen.

9. The adaptive analytical instrument of claim 1, wherein the target-analyte is carbon-dioxide.

10. The adaptive analytical instrument of claim 1, wherein the target-analyte is water vapor.

11. The adaptive analytical instrument of claim 1, wherein the duration of future sensing periods is set at an increased duration when the value of the at least one previous target-analyte transmission rate measurement is above a predetermined threshold value, and set at a decreased duration when the value of the at least one previous target-analyte transmission rate measurement is below a predetermined threshold value.

12. The adaptive analytical instrument of claim 1, wherein the duration of sensing periods is set at an initial duration and the initial duration is increased when the value of the at least one previous target-analyte transmission rate measurement is above a predetermined threshold value.

13. The adaptive analytical instrument of claim 1, wherein the value of at least one previous target-analyte transmission rate measurement is the value of the immediately preceding measurement.

14. The adaptive analytical instrument of claim 1, wherein the value of at least one previous target-analyte transmission rate measurement is the mean or median of a plurality of immediately preceding measurements.

15. The adaptive analytical instrument of claim 2, wherein the target-analyte is oxygen.

16. The adaptive analytical instrument of claim 2, wherein the target-analyte is carbon-dioxide.

17. The adaptive analytical instrument of claim 2, wherein the target-analyte is water vapor.

18. The adaptive analytical instrument of claim 2, wherein the value of at least one previous target-analyte transmission rate measurement is the value of the immediately preceding measurement.

19. The adaptive analytical instrument of claim 2, wherein the value of at least one previous target-analyte transmission rate measurement is the mean or median of a plurality of immediately preceding measurements.

20. The adaptive analytical instrument of claim 3, wherein the target-analyte is oxygen.

21. The adaptive analytical instrument of claim 3, wherein the target-analyte is carbon-dioxide.

22. The adaptive analytical instrument of claim 3, wherein the target-analyte is water vapor.

23. The adaptive analytical instrument of claim 3, wherein the frequency of future rezeros is set at a decreased frequency when the value of the at least one previous target-analyte transmission rate measurement is above a predetermined threshold value, and set at an increased frequency when the value of the at least one previous target-analyte transmission rate measurement is below a predetermined threshold value.

24. The adaptive analytical instrument of claim 3, wherein the frequency of future rezeros is set at an initial frequency and the initial frequency is decreased when the value of the at least one previous target-analyte transmission rate measurement is above a predetermined threshold value.

25. The adaptive analytical instrument of claim 3, wherein the value of at least one previous target-analyte transmission rate measurement is the value of the immediately preceding measurement.

26. The adaptive analytical instrument of claim 3, wherein the value of at least one previous target-analyte transmission rate measurement is the mean or median of a plurality of immediately preceding measurements.

27. The adaptive analytical instrument of claim 4, wherein the target-analyte is oxygen.

28. The adaptive analytical instrument of claim 4, wherein the target-analyte is carbon-dioxide.

29. The adaptive analytical instrument of claim 4, wherein the target-analyte is water vapor.

30. The adaptive analytical instrument of claim 4, wherein the ascertained target-analyte transmission rate of the test film is the value of the final measurement.

31. The adaptive analytical instrument of claim 4, wherein the ascertained target-analyte transmission rate of the test film is the mean or median of a plurality of consecutive measurements taken at conclusion of the permeation testing period.

32. A method of measuring target-analyte transmission rate of a test film, comprising the steps of:
    (a) obtaining a computer controlled target-analyte permeation testing instrument according to claim 1,
    (b) obtaining a test film, and
    (c) ascertaining the target-analyte transmission rate of the test film using the computer controlled target-analyte permeation testing instrument without user input or selection of a sensing period duration.

33. A method of measuring target-analyte transmission rate of a test film, comprising the steps of:
    (a) obtaining a computer controlled target-analyte permeation testing instrument according to claim 2,
    (b) obtaining a test film, and
    (c) ascertaining the target-analyte transmission rate of the test film using the computer controlled target-analyte permeation testing instrument without user input or selection of a frequency of rezeros.

34. A method of measuring target-analyte transmission rate of a test film, comprising the steps of:
    (a) obtaining a computer controlled target-analyte permeation testing instrument according to claim 3,
    (b) obtaining a test film, and
    (c) ascertaining the target-analyte transmission rate of the test film using the computer controlled target-analyte permeation testing instrument without user input or selection of a frequency of rezeros.

35. A method of measuring target-analyte transmission rate of a test film, comprising the steps of:
    (a) obtaining a computer controlled target-analyte permeation testing instrument according to claim 4,
    (b) obtaining a test film, and
    (c) ascertaining the target-analyte transmission rate of the test film using the computer controlled target-analyte permeation testing instrument without user input establishing whether to perform an individual zero.

\* \* \* \* \*